United States Patent
Ginosar et al.

(10) Patent No.: US 9,815,747 B2
(45) Date of Patent: Nov. 14, 2017

(54) SYNGAS CONVERSION TO A LIGHT ALKENE AND RELATED METHODS

(71) Applicant: BATTELLE ENERGY ALLIANCE, LLC, Idaho Falls, ID (US)

(72) Inventors: Daniel M Ginosar, Idaho Falls, ID (US); Lucia M Petkovic, Idaho Falls, ID (US)

(73) Assignee: Battelle Energy Alliance, LLC, Idaho Falls, ID (US)

( * ) Notice: Subject to any disclaimer, the term of this patent is extended or adjusted under 35 U.S.C. 154(b) by 0 days.

(21) Appl. No.: 15/098,678

(22) Filed: Apr. 14, 2016

(65) Prior Publication Data
US 2016/0318823 A1 Nov. 3, 2016

Related U.S. Application Data (60) Provisional application No. 62/153,855, filed on Apr. 28, 2015.

(51) Int. Cl.
| | |
|---|---|
| *C07C 1/04* | (2006.01) |
| *B01J 23/30* | (2006.01) |
| *B01J 37/08* | (2006.01) |

(52) U.S. Cl.
CPC .............. *C07C 1/043* (2013.01); *B01J 23/30* (2013.01); *B01J 37/08* (2013.01); *C07C 1/0445* (2013.01); *C07C 2521/06* (2013.01); *C07C 2523/30* (2013.01); *Y02P 20/52* (2015.11)

(58) Field of Classification Search
None
See application file for complete search history.

(56) References Cited

U.S. PATENT DOCUMENTS

| | | |
|---|---|---|
| 4,255,349 A | 3/1981 | Butter et al. |
| 6,602,921 B2 | 8/2003 | Manzer et al. |
| 7,973,087 B2 | 7/2011 | Kibby et al. |
| 8,445,550 B2 | 5/2013 | Jothimurugesan et al. |
| 8,519,011 B2 | 8/2013 | Saxton et al. |
| 8,865,613 B2 | 10/2014 | Mordkovich et al. |
| 8,916,661 B2 | 12/2014 | Bradin |

(Continued)

FOREIGN PATENT DOCUMENTS

| | | |
|---|---|---|
| WO | 2015015313 A2 | 2/2015 |
| WO | 2015015316 A2 | 2/2015 |

OTHER PUBLICATIONS

Wang, et al., "Review of Directly Producing Light Olefins via CO Hydrogenation", Journal of Natural Gas Chemistry vol. 12, No. 1, 2003, pp. 10-16.

*Primary Examiner* — Medhanit Bahta
(74) *Attorney, Agent, or Firm* — TraskBritt (57) ABSTRACT

Methods of producing a light alkene. The method comprises contacting syngas and tungstated zirconia to produce a product stream comprising at least one light alkene. The product stream is recovered. Methods of converting syngas to a light alkene are also disclosed. The method comprises heating a precursor of tungstated zirconia to a temperature of between about 350° C. and about 550° C. to form tungstated zirconia. Syngas is flowed over the tungstated zirconia to produce a product stream comprising at least one light alkene and the product stream comprising the at least one light alkene is recovered.

20 Claims, 5 Drawing Sheets

(56) References Cited

U.S. PATENT DOCUMENTS

| | | | |
|---|---|---|---|
| 2002/0028853 A1* | 3/2002 | Manzer | B01J 23/8913 |
| | | | 518/713 |
| 2003/0105171 A1 | 6/2003 | Subramanian et al. | |
| 2007/0244000 A1 | 10/2007 | Molinier et al. | |
| 2011/0257007 A1* | 10/2011 | Khurshid | B01J 21/066 |
| | | | 502/308 |
| 2013/0036660 A1 | 2/2013 | Woods et al. | |
| 2013/0109768 A1 | 5/2013 | Saxton et al. | |
| 2013/0263498 A1 | 10/2013 | Kania et al. | |
| 2014/0128486 A1 | 5/2014 | Karim et al. | |

* cited by examiner

SYNGAS CONVERSION TO A LIGHT ALKENE AND RELATED METHODS

CROSS-REFERENCE TO RELATED APPLICATION

This application claims the benefit of U.S. Provisional Patent Application Ser. No. 62/153,855, filed Apr. 28, 2015, the disclosure of which is hereby incorporated herein in its entirety by this reference.

STATEMENT REGARDING FEDERALLY SPONSORED RESEARCH OR DEVELOPMENT

This invention was made with government support under Contract Number DE-AC07-05ID14517 awarded by the United States Department of Energy. The government has certain rights in the invention.

TECHNICAL FIELD

The disclosure, in various embodiments, relates to methods for converting syngas to a light alkene. More specifically, embodiments of the disclosure relate to methods for directly converting syngas to a light alkene, such as ethylene, propylene, butylene, or combinations thereof.

BACKGROUND

The Fischer-Tropsch process is known in the art to convert synthetic gas (syngas) to hydrocarbon compounds using a catalyst, such as a metal or metal oxide catalyst. Syngas is a mixture of hydrogen ($H_2$) and carbon monoxide (CO). The hydrocarbon compounds produced by the Fischer-Tropsch process include a mixture of compounds having between one carbon atom ($C_1$) and greater than twenty carbon atoms ($C_{20+}$), such as $C_{50}$ or $C_{100}$ or greater. The hydrocarbon compounds include methane, other alkanes, alkenes, aliphatic alcohols, and other oxygenated hydrocarbon compounds. For some intended uses, certain hydrocarbon compounds are desired as the predominant products of the Fischer-Tropsch process. Some Fischer-Tropsch processes have been found to selectively produce $C_{20+}$, $C_{11+}$, $C_{5+}$, or $C_{2-4}$ hydrocarbon compounds, while other Fischer-Tropsch processes have been found to selectively produce methane. For instance, iron-, cobalt-, nickel-, or ruthenium-based catalysts are known in the art to produce high levels of $C_{5+}$ hydrocarbon compounds with low levels of $C_{1-4}$ hydrocarbon compounds.

Ethylene, propylene (also known as propene), and butylene (also known as butene) are among the alkenes produced by the Fischer-Tropsch process. Ethylene and propylene are important reagents in the petrochemical industry because they are the monomers used in the production of many plastics. Ethylene is polymerized to make low and high density polyethylene products, such as for plastic films, containers, or coatings, while propylene is used to make polypropylene, acrylonitrile, or propylene oxide. Butylene is also used in the production of plastics, such as being polymerized to make polybutylene.

Multi-step processes of forming ethylene or propylene are known in the art. In one process, syngas is converted to methanol and dimethyl ether, which are converted to ethylene and propylene. In this process, a dual-component catalyst is used that includes a metal oxide component and a molecular sieve component. The syngas is converted to methanol and dimethyl ether by the metal oxide component, and the methanol and dimethyl ether are converted to ethylene and propylene by the molecular sieve component. In another process, syngas is converted to methanol, which is converted to ethylene or propylene. While these processes produce ethylene and propylene, they require significant capital and operating costs.

BRIEF SUMMARY

An embodiment of the disclosure includes a method of producing a light alkene that comprises contacting syngas and tungstated zirconia to produce a product stream comprising at least one light alkene. The product stream is recovered.

Another embodiment of the disclosure includes a method of converting syngas to a light alkene that comprises heating a precursor of tungstated zirconia to a temperature of between about 350° C. and about 550° C. to form tungstated zirconia. Syngas is flowed over the tungstated zirconia to produce a product stream comprising at least one light alkene. The product stream comprising the at least one light alkene is recovered.

DETAILED DESCRIPTION

A light alkene is produced from syngas by a catalytic process. The light alkene is directly produced from the syngas using tungstated zirconia as a catalyst. The tungstated zirconia and syngas are contacted with one another under appropriate reaction conditions, directly converting the syngas to the light alkene. The light alkene is selectively formed by the catalytic process and accounts for greater than about 50% by weight (wt %) of a total weight of hydrocarbon compounds produced by the syngas conversion. Thus, a process for directly producing the light alkene is disclosed.

As used herein, the term "light alkene" means and includes ethylene ($C_2H_4$), propylene ($C_3H_6$), butylene ($C_4H_8$), or combinations thereof. The butylene may include 1-butylene or 2-butylene.

As used herein, the term "syngas" means and includes a mixture of hydrogen ($H_2$) and carbon monoxide (CO).

As used herein, the terms "directly produced," "directly converted," or other word forms mean and include forming the light alkene from syngas without first forming another stable intermediate.

As used herein, the term "tungstated zirconia" means and includes zirconia ($ZrO_2$) modified with tungsten oxide ($WO_x$), where x is 2 or 3.

The following description provides specific details, such as equipment types, material compositions, and processing conditions in order to provide a thorough description of embodiments of the disclosure. However, a person of ordinary skill in the art will understand that the embodiments of the disclosure may be practiced without employing these specific details. Indeed, the embodiments of the disclosure may be practiced in conjunction with conventional systems and methods employed in the industry. In addition, only those method components and acts necessary to understand the embodiments of the disclosure are described in detail below. A person of ordinary skill in the art will understand that some system components (e.g., pipelines, pumps, line filters, valves, temperature detectors, pressure detectors, and the like) are not described herein but that using various conventional system components and acts would be in accord with the disclosure.

The syngas is converted to the light alkene according to the reaction below:

$$2nH_2 + nCO \rightarrow C_nH_{2n} + nH_2O,$$

where n is 2, 3, or 4. The conversion of the syngas to the light alkene may be conducted by contacting the syngas and tungstated zirconia under appropriate reaction conditions for the syngas to be converted into the light alkene. To form the light alkene, the syngas may be introduced into a reaction zone of a reactor containing the tungstated zirconia.

The syngas used in the syngas conversion may be produced from a variety of carbon sources including, but not limited, to biomass, natural gas, $C_1$-$C_5$ hydrocarbons, naphtha, heavy petroleum oils, or coal. The syngas may be produced by conventional techniques, such as partial oxidation, steam reforming, or $CO_2$ reforming, which are not described in detail herein. The syngas may be substantially pure or may include a diluent gas, such as carbon dioxide ($CO_2$), nitrogen ($N_2$), methane, or steam. The diluent gas may be inert (i.e., non-reactive) or a reaction product of the conversion reaction. However, trace amounts of contaminants (i.e., impurities) may be present in the syngas. The syngas may include a molar ratio of hydrogen:carbon monoxide ($H_2$:CO) of from about 0.5:1 to about 20:1, such as from about 1:1 to about 10:1, from about 1:1 to about 5:1, from about 1:1 to about 4:1, or from about 1:1 to about 3:1.

The tungstated zirconia ($WO_x$—$ZrO_2$) may be produced  by conventional techniques, which are not described in detail herein. By way of example only, a zirconium oxide precursor, a tungsten oxide precursor, and a solvent may be combined and the solvent removed to absorb the tungsten oxide precursor onto the zirconium oxide precursor and form a precursor of the tungstated zirconia. By way of example only, the zirconium oxide precursor may be zirconium hydroxide ($Zr(OH)_4$), zirconyl chloride octahydrate ($ZrOCl_2.8H_2O$), or zirconium nitrate ($Zr(NO_3)_4$). The zirconium oxide precursor may be an amorphous form, such as amorphous zirconium hydroxide. By way of example only, the tungsten precursor may be ammonium tungstate (($NH_4$)$_{10}$$H_2$($W_2O_7$)$_6$), ammonium metatungstate (($NH_4$)$_6$[$H_2W_{12}O_{40}$].$nH_2O$), or tungsten chloride ($WCl_6$). Before use in the syngas conversion, the precursor of the tungstated zirconia may be heated (i.e., calcined) in air or nitrogen ($N_2$) to form the tungstated zirconia having tungsten oxide species on the surface of the zirconia. After calcination, the amorphous form of the zirconium oxide is crystallized. Alternatively, the tungstated zirconia may be formed by absorbing the tungsten oxide precursor onto zirconium oxide that is already crystallized. The tungstated zirconia may include the tungsten oxide at a tungsten loading of from about 1 wt % to about 18 wt % of a total weight of the tungstated zirconia, such as from about 5 wt % to about 17 wt % or from about 10 wt % to about 16 wt %. In one embodiment, the tungstated zirconia includes about 15.75 wt % of the tungsten oxide.

The calcination temperature may be between about 325° C. and about 610° C., such as between about 350° C. and about 550° C., between about 375° C. and about 500° C., between about 350° C. and about 450° C., between about 350° C. and about 425° C., or between about 450° C. and about 500° C. In one embodiment, the calcination temperature is 450° C. In another embodiment, the calcination temperature is 475° C. In yet another embodiment, the calcination temperature is 500° C. The precursor of the tungstated zirconia may be exposed to the calcination temperature for an amount of time sufficient to convert the amorphous zirconium to crystalline zirconium, such as from about 0.5 hour to about 8 hours. Following the calcination, a portion of the surface of the zirconia is modified with the tungsten oxide.

The precursor of the tungstated zirconia may also be purchased commercially, such as from MEL Chemicals Inc. (Flemington, N.J.). The as-received precursor of the tungstated zirconia may be calcined, as described above, before use to produce the tungstated zirconia.

The syngas may be flowed into the reaction zone of the reactor to convert the syngas into the light alkene. The tungstated zirconia may be contained in a catalyst bed in the reaction zone of the reactor. The amount of tungstated zirconia to be used in the reactor may depend on the flow rate of syngas and desired production rate of the light alkene. The reactor may include, but is not limited to, a fixed bed reactor, a fluid bed reactor, a moving bed reactor, a hybrid reactor with a dense bed, fixed bed, or fast-fluidized bed reaction zone, a circulating fluidized bed reactor, or a riser reactor. Such reactors are known in the art and, therefore, are not described in detail herein.

During the syngas conversion, the reaction zone of the reactor may be maintained at appropriate temperature and pressure conditions for the syngas to be converted into the light alkene. The syngas and tungstated zirconia may be contacted in the reaction zone at a temperature (i.e., a conversion temperature) between about 150° C. and about 550° C., such as between about 200° C. and about 500° C., between about 250° C. and about 450° C., between about 300° C. and about 400° C., or between about 325° C. and about 375° C. In one embodiment, the conversion temperature is 350° C. The pressure within the reactor may be maintained at from about 500 psig (about 3.45 MPa) to about 600 psig (about 4.14 MPa), such as about 570 psig (about 3.93 MPa). In one embodiment, the pressure is 570 psig (3.93 MPa). However, other temperatures and pressures may be used to convert the syngas into the light alkene.

The gas hourly space velocity of the syngas may also be appropriately selected during the syngas conversion. The gas hourly space velocity is a ratio between the flow rate of the syngas and a mass of the tungstated zirconia catalyst used in the syngas conversion. The gas hourly space velocity may range from about 300 standard liters per hour per kilogram of catalyst (SLPH/kg) to about 1,800 SLPH/kg of catalyst. In one embodiment, the gas hourly space velocity is 408 SLPH/kg of catalyst. In another embodiment, the gas hourly space velocity is 1,620 SLPH/kg of catalyst.

Following the syngas conversion, a product stream including the light alkene is produced. The light alkene may be produced in a gaseous form, which is recovered as described in more detail below. The light alkene may account for greater than about 50 wt % of the hydrocarbon compounds produced by the syngas conversion, such as greater than about 60 wt % of the hydrocarbon compounds or greater than about 70 wt % of the total weight of the hydrocarbon compounds produced. The product stream may also include other hydrocarbon compounds including, but not limited to, methane; linear, branched, or cyclic alkane compounds having between 2 carbon atoms and 4 carbon atoms; linear, branched, or cyclic alkane or alkene compounds having greater than or equal to 5 carbon atoms; aliphatic alcohols; other oxygenated hydrocarbon compounds; or combinations thereof. In one embodiment, the light alkene accounts for about 75 wt % of the hydrocarbon compounds produced by the syngas conversion. Thus, the light alkene selectivity for the syngas conversion is about 75%.

The product stream including the light alkene may exit the reactor and be recovered. The light alkene may be recovered from the other hydrocarbon compounds in the product stream by conventional techniques, such as by distillation or fractionation, which are not described in detail herein. Individual light alkenes, such as ethylene, propylene, or butylene, may be separated and recovered from each other and from the other hydrocarbon compounds of the product stream. The individual light alkenes may be further purified to remove by-products or contaminants before use. The separation and purification may be conducted by conventional techniques, which are not described in detail herein.

The product stream including the light alkene, such as ethylene, propylene, butylene, or combinations thereof, may be polymerized in the gas phase to form polyolefins, such as polyethylene, polypropylene, or polybutylene. The polymerization may be conducted by conventional techniques, which are not described in detail herein. Alternatively, the light alkene may be used as a reagent in other chemical reactions. Each of the other hydrocarbon compounds may be recovered from the product stream and used in any conventional use or as a reagent in other chemical reactions. For instance, the methane may be recovered and used as a fuel or as a reagent in other chemical reactions.

By using tungstated zirconia as the catalyst and appropriately selecting the calcination temperature during production of the tungstated zirconia, the syngas may be directly converted to the light alkene. Thus, a single act is used to produce the light alkene from the syngas, reducing the capital and operating costs of the process relative to the multiple act processes known in the art.

As described in more detail below, the rate of syngas conversion may be affected by changes in the conversion temperature. For instance, the rate of syngas conversion may be increased by increases in the conversion temperature. By way of example only, the syngas conversion may be increased at a conversion temperature of between about 350° C. and about 425° C.

The rate of syngas conversion and light alkene selectivity may also be affected by changes in the syngas flow rate. For instance, the rate of syngas conversion and light alkene selectivity may be increased at increased flow rate and increased gas hourly space velocity. By way of example only, the rate of syngas conversion may be doubled by increasing the flow rate of the synthesis gas.

The rate of syngas conversion and light alkene selectivity may also be affected by appropriately selecting the calcination temperature of the tungstated zirconia. For instance, the rate of syngas conversion and light alkene selectivity may be increased at a calcination temperature of between about 450° C. and about 500° C. compared to lower or higher calcination temperatures. Without being bound to any theory, it is believed that the calcination temperature affects the number, density, and strength of acid sites on the surface of the zirconia, the crystal structure of the zirconia, the surface area of the tungstated zirconia, or the surface structure of the tungstated zirconia.

The light alkene selectivity of the syngas conversion may also be affected by the $H_2$:CO ratio of the syngas used in the syngas conversion. The light alkene selectivity may be increased using syngas having a $H_2$:CO ratio of greater than about 1:1. For instance, using syngas having a $H_2$:CO ratio of between about 1.2:1 to about 4:1, such as about 2:1 or about 3:1, may increase the light alkene selectivity compared to syngas having a $H_2$:CO ratio of about 1:1. Thus, the desired light alkene selectivity may be achieved by appropriately selecting the $H_2$:CO ratio of the syngas. The increased $H_2$:CO ratio may also decrease deactivation of the tungstated zirconia.

The following examples serve to explain embodiments of the disclosure in more detail. These examples are not to be construed as being exhaustive or exclusive as to the scope of this disclosure.

EXAMPLES

Experiments determining the conversion of the syngas to the light alkene were conducted at a tungstated zirconia calcination temperature of 500° C., a conversion temperature of 350° C., a pressure of 570 psig, a 25 standard cubic centimeters per minute (sccm) syngas feed, and a $H_2$:CO ratio of 1:1 unless otherwise noted. The syngas was introduced into a reactor including the tungstated zirconia, and the CO conversion, light alkene selectivity, average production rate, hydrocarbon production, and coke deposition were measured by conventional techniques.

Example 1

Figure 1:
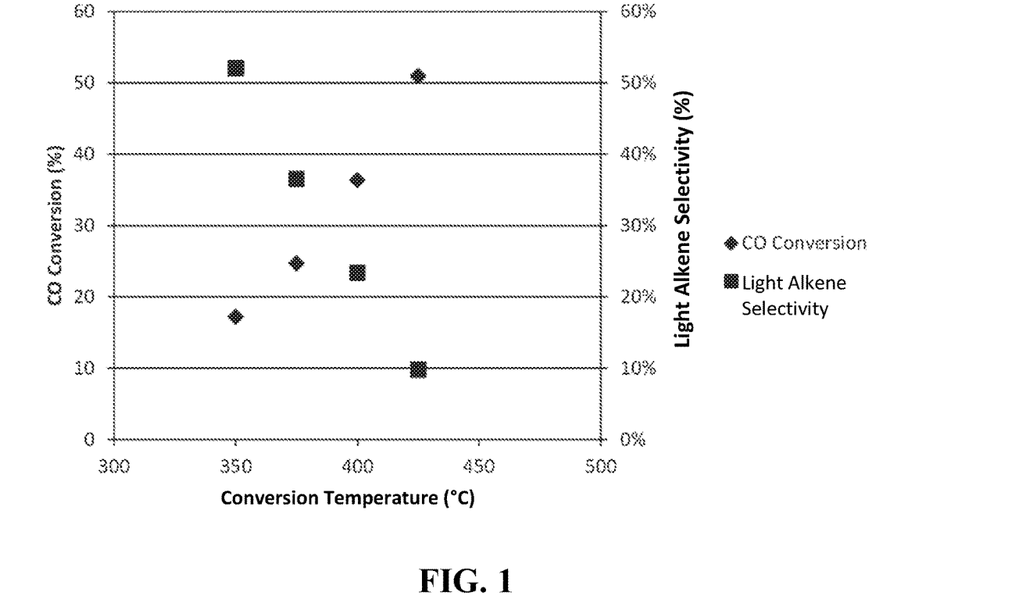
FIG. 1 is a plot of CO conversion and light alkene selectivity as a function of conversion temperature.

The effect of temperature on the syngas conversion and alkene selectivity were determined. The conversion temperature was varied between 350° C. and 425° C. while other reaction conditions (570 psig, 25 sccm syngas feed, $H_2$:CO=1:1, catalyst calcination 400° C.) were held constant. A plot of the percentage of CO conversion and percentage of alkene selectivity as a function of temperature is shown in FIG. 1. The CO conversion increased about three fold between 350° C. and 425° C., from about 17% at 350° C. to over 50% at 425° C. The hydrocarbon production (not shown) increased about 15 times over the same temperature range. However, the alkene selectivity decreased over the temperature range, from about 54% at 350° C. to about 10% at 425° C. Additional experiments were conducted at a conversion temperature of 350° C. since the alkene selectivity was highest at this temperature.

Example 2

Figure 2:
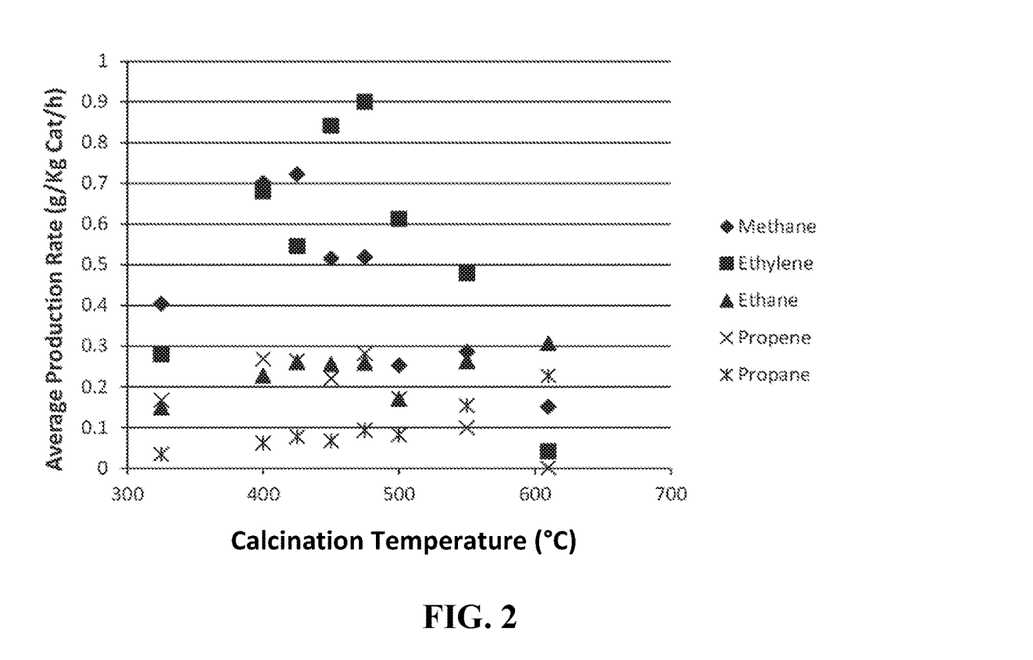
FIG. 2 is a plot of average production rate as a function of catalyst calcination temperature of tungstated zirconia.

The effect of tungstated zirconia calcination temperature on the average production rate of methane, ethylene, ethane, propylene, and propane, hydrocarbon production, and percentage of alkene selectivity were determined. The catalyst calcination temperature was varied between 325° C. and 610° C. while other reaction conditions (350° C. conversion temperature, 570 psig, 25 sccm syngas feed, $H_2$:CO=1:1) were held constant. As shown in FIG. 2, ethylene production generally increased with calcination temperatures between about 325° C. and about 475° C., then decreased at a temperature above 475° C. Propylene production followed a similar trend, increasing with calcination temperatures between about 325° C. and about 475° C., then decreasing at a temperature above 475° C.

Figure 3:
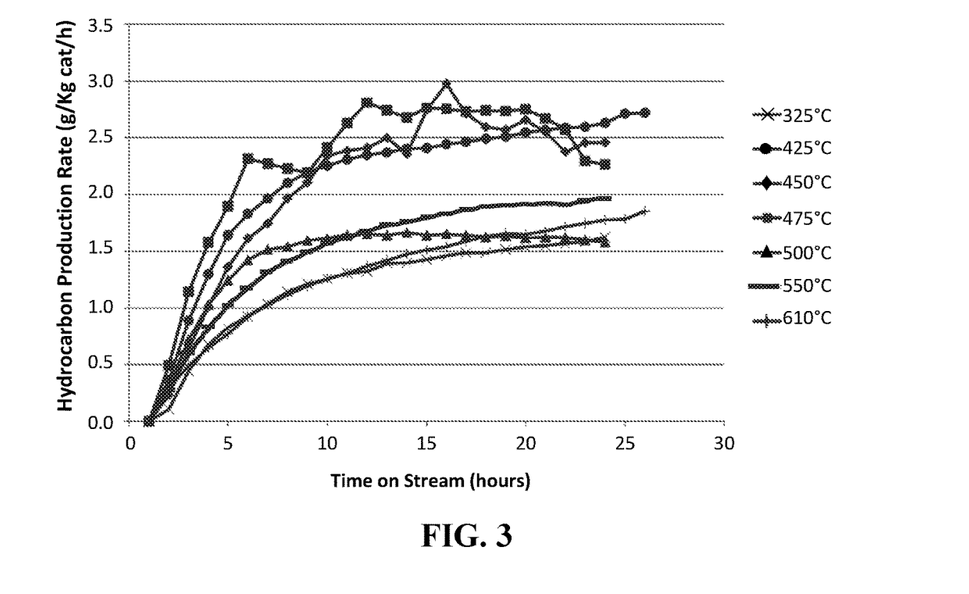
FIG. 3 is a plot of hydrocarbon production as a function of time on stream for catalyst calcination temperatures between 325° C. and 610° C.

The effect of tungstated zirconia calcination temperature on hydrocarbon production is shown in FIG. 3. Increased hydrocarbon production rates were observed at a tungstated zirconia calcination temperature between about 425° C. and about 475° C. At higher calcination temperatures, the hydrocarbon production rate decreased.

Figure 4:
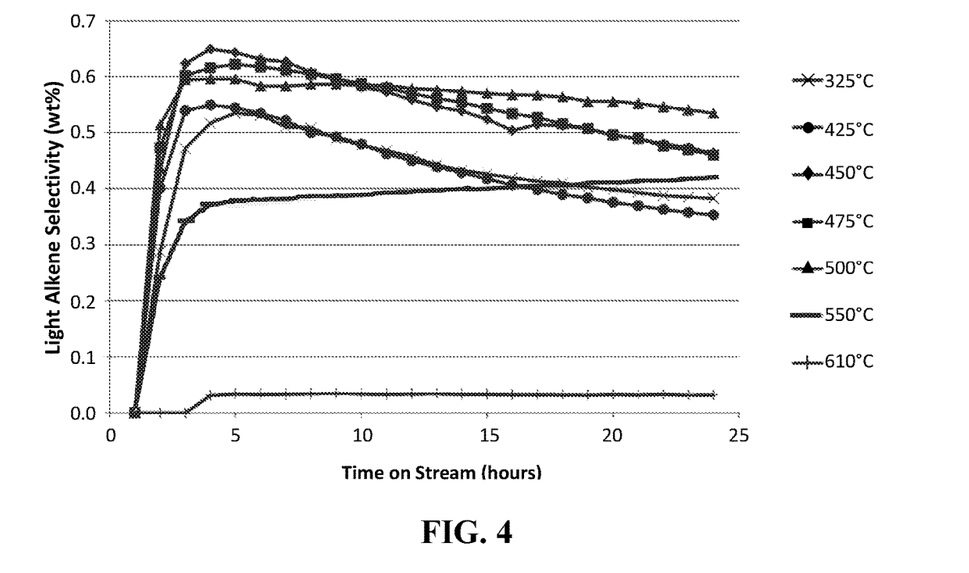
FIG. 4 is a plot of light alkene selectivity as a function of time on stream for catalyst calcination temperatures between 325° C. and 610° C.

The effect of tungstated zirconia calcination temperature on alkene selectivity is shown in FIG. 4. Increased alkene selectivities were observed at a tungstated zirconia calcination temperature of from about 450° C. to about 500° C. At higher calcination temperatures, the alkene selectivity decreased dramatically.

The catalytic performance of the tungstated zirconia calcined at different temperatures was measured. The total acidity (acid site densities) and strong acidity were measured by conventional techniques and are shown in Table 1.

TABLE 1

Catalytic Performance of the Tungstated Zirconia Catalyst.

| Calcination Temperature (° C.) | Total Acidity (μmol/g) | Strong Acidity (μmol/g) |
|---|---|---|
| 400 | 819 | 461 |
| 500 | 543 | 330 |
| 660 | 374 | 225 |
| 800 | 236 | 125 |

Example 3

Figure 5:
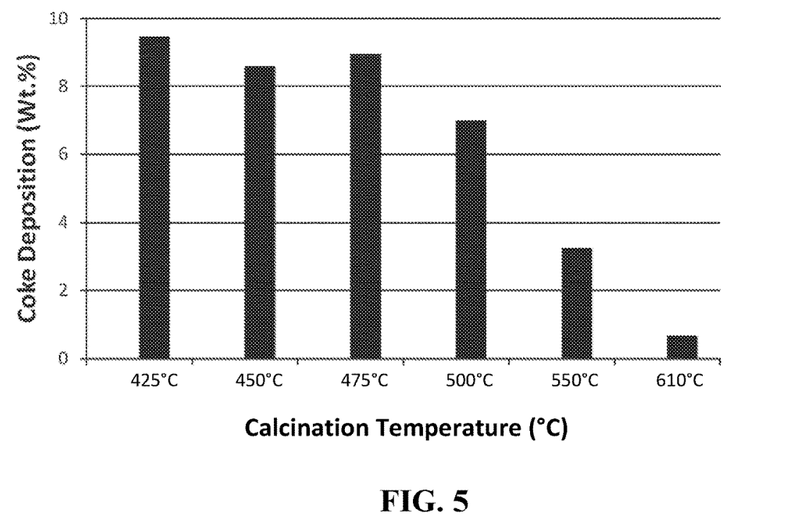
FIG. 5 is a plot of coke deposition as a function of the catalyst calcination temperature of tungstated zirconia.

The effect of calcination temperature on coke deposition on the tungstated zirconia was determined by conventional techniques. The calcination temperature of the tungstated zirconia was varied between 425° C. and 610° C. while other reaction conditions (350° C. conversion temperature, 570 psig, 25 sccm syngas feed, $H_2$:CO=1:1) were held constant. The amount of coke deposition on the tungstated zirconia was measured after 24 hours of reaction time. As shown in FIG. 5, coke deposition between 7% and 10% was observed at calcination temperatures between about 425° C. and about 500° C. Lower amounts of coke deposition were observed at temperatures of 550° C. and 610° C.

Example 4

Figure 6:
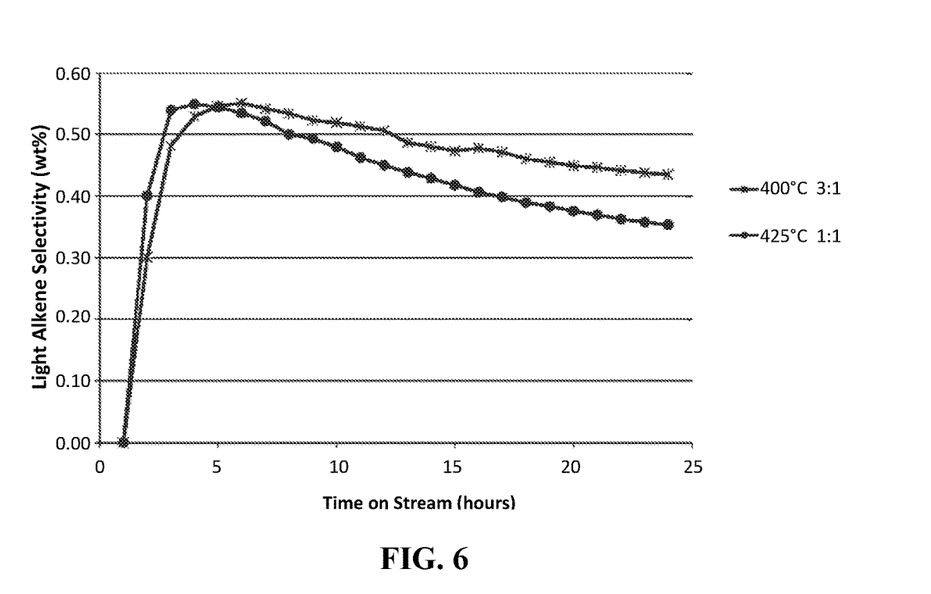
FIG. 6 is a plot of light alkene selectivity as a function of time on stream for tungstated zirconia having different calcination temperature and different syngas flow rates.

The effect of increased $H_2$:CO ratio on the light alkene selectivity was determined by conventional techniques. The tungstated zirconia was calcined at a temperature of 425° C. or 400° C. and the reaction conditions of 350° C. conversion temperature, 570 psig, and 25 sccm syngas feed were held constant. The $H_2$:CO ratio was increased from 1:1 to 3:1, respectively. As shown in FIG. 6, the light alkene selectivity increased at the higher $H_2$:CO ratio of 3:1 and a 400° C. tungstated zirconia calcination temperature compared to a $H_2$:CO ratio of 1:1 and a 425° C. tungstated zirconia calcination temperature.

Figure 7:
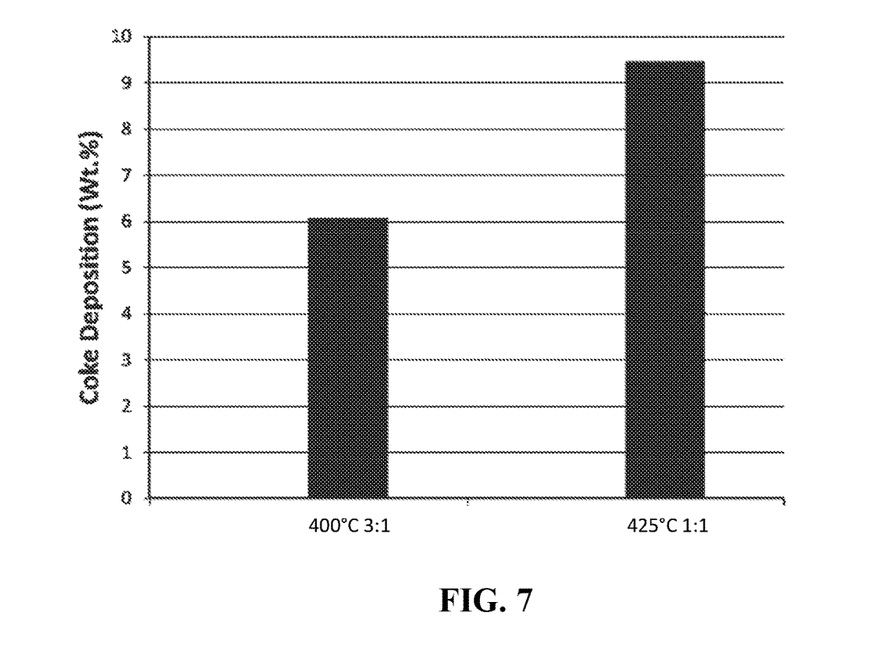
FIG. 7 is a plot of coke deposition as a function of different tungstated zirconia calcination temperatures and different syngas flow rates.

The effect of increased $H_2$:CO ratio on coke deposition was also determined by conventional techniques. The $H_2$:CO ratio was increased from 1:1 to 3:1 at a tungstated zirconia calcination temperature of 400° C. or 425° C., respectively. The conversion temperature, pressure, and flow rate of syngas were held constant at 350° C., 570 psig, and 25 sccm, respectively. As shown in FIG. 7, coke deposition decreased from 9.5 wt % to 6.1 wt %, a 36% reduction, at the higher $H_2$:CO ratio.

Example 5

Figure 8:
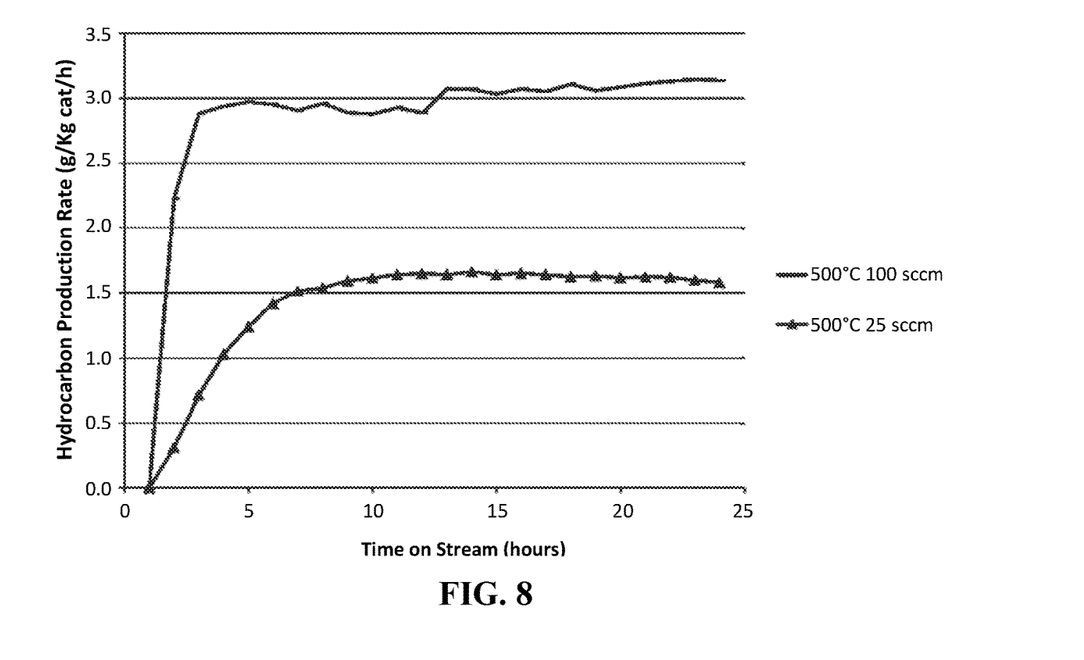
FIG. 8 is a plot of hydrocarbon production as a function of time on stream for tungstated zirconia having different calcination temperature and different syngas flow rates.

The effect of increased syngas flow rate on the hydrocarbon production was determined by conventional techniques. The flow rate of the syngas was increased from 25 sccm to 100 sccm (the gas hourly space velocity increased from 408 SLPH/kg of catalyst to 1,620 SLPH/kg of catalyst) while other reaction conditions (350° C. conversion temperature, 500° C. catalyst calcination temperature, 570 psig, $H_2$:CO=1:1) were held constant. Using the higher syngas flow rate (100 sccm), the hydrocarbon production increased from about 1.5 g/Kg cat./hr to over 3.0 g/Kg cat./hr, as shown in FIG. 8.

Figure 9:
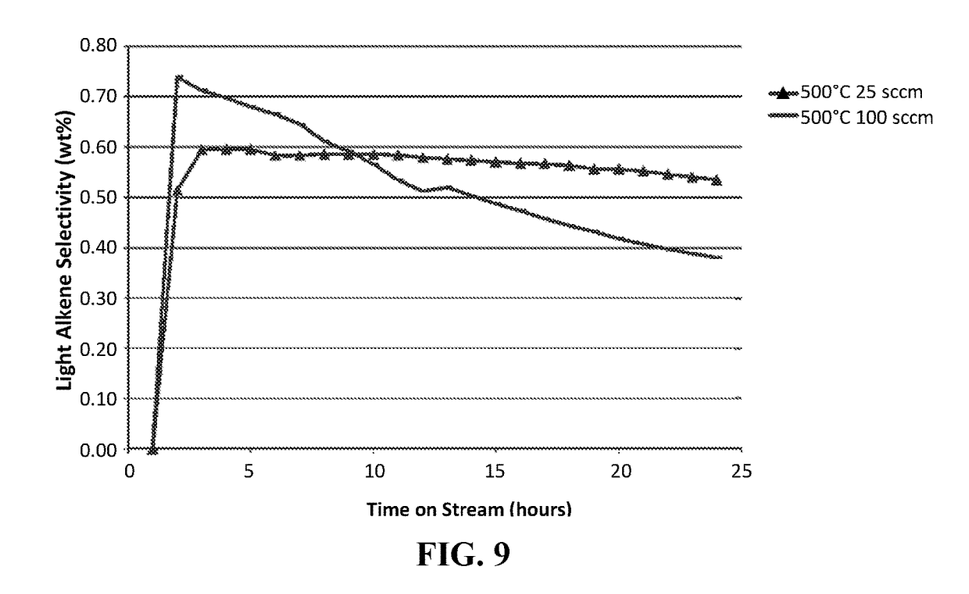
FIG. 9 is a plot of light alkene selectivity as a function of time on stream for tungstated zirconia having different calcination temperature and different syngas flow rates.

The effect of increased syngas flow rate on the light alkene selectivity was also determined by conventional techniques. The syngas flow rate was increased from 25 sccm to 100 sccm (the gas hourly space velocity increased from 408 SLPH/kg of catalyst to 1,620 SLPH/kg of catalyst) while other reaction conditions (350° C. conversion temperature, 500° C. catalyst calcination temperature, 570 psig, $H_2$:CO=1:1) were held constant. With the higher syngas flow rate (100 sccm), the light alkene selectivity was about 75% compared to 60% for the lower syngas flow rate (25 sccm), as shown in FIG. 9.

Thus, the hydrocarbon production rate and light alkene selectivity increased with increased syngas flow rate.

The embodiments of the disclosure described above and illustrated in the accompanying drawings do not limit the scope of the disclosure, since these embodiments are merely examples of embodiments of the disclosure. The disclosure is defined by the appended claims and their legal equivalents. Any equivalent embodiments lie within the scope of this disclosure. Indeed, various modifications of the disclosure, in addition to those shown and described herein, such as alternative useful combinations of the elements described, will become apparent to those of ordinary skill in the art from the description. Such modifications and embodiments also fall within the scope of the appended claims and their legal equivalents.

What is claimed is:

1. A method of producing a light alkene comprising:
   contacting a catalyst consisting of tungstated zirconia with syngas to produce a product stream comprising at least one light alkene; and
   recovering the product stream.

2. The method of claim 1, wherein contacting a catalyst consisting of tungstated zirconia with syngas comprises contacting the catalyst comprising from about 5% by weight to about 17% by weight tungsten oxide with the syngas.

3. The method of claim 1, wherein contacting a catalyst consisting of tungstated zirconia with syngas comprises contacting the catalyst with the syngas at a temperature of between about 250° C. and about 450° C.

4. The method of claim 1, wherein contacting a catalyst consisting of tungstated zirconia with syngas comprises contacting the catalyst with the syngas at a temperature of about 350° C.

5. The method of claim 1, wherein contacting a catalyst consisting of tungstated zirconia with syngas to produce a product stream comprising at least one light alkene comprises producing a product stream comprising ethylene, propylene, butylene, or combinations thereof.

6. The method of claim 1, wherein contacting a catalyst consisting of tungstated zirconia with syngas to produce a product stream comprising at least one light alkene comprises producing the at least one light alkene at greater than about 50% by weight of a total weight of the product stream.

7. The method of claim 1, wherein contacting a catalyst consisting of tungstated zirconia with syngas to produce a product stream comprising at least one light alkene comprises producing the at least one light alkene at greater than about 60% by weight of a total weight of the product stream.

8. The method of claim 1, wherein contacting a catalyst consisting of tungstated zirconia with syngas to produce a product stream comprising at least one light alkene comprises producing the at least one light alkene at greater than about 70% by weight of a total weight of the product stream.

9. The method of claim 1, wherein contacting a catalyst consisting of tungstated zirconia with syngas to produce a product stream comprising at least one light alkene comprises directly producing ethylene, propylene, butylene, or combinations thereof from the syngas.

10. A method of converting syngas to a light alkene, comprising:
heating a precursor of tungstated zirconia in air or nitrogen to a temperature of between about 350° C. and about 550° C. to form tungstated zirconia;
flowing syngas over the tungstated zirconia to produce a product stream comprising at least one light alkene; and
recovering the product stream comprising the at least one light alkene wherein heating a precursor of tungstated zirconia comprises forming the tungstated zirconia comprising tungsten oxide at from about 5% by weight to about 17% by weight of a total weight of the tungstated zirconia.

11. The method of claim 10, wherein heating a precursor of tungstated zirconia in air or nitrogen to a temperature of between about 350° C. and about 550° C. comprises heating the precursor of tungstated zirconia in air or nitrogen to a temperature of between about 450° C. and about 500° C. to form the tungstated zirconia.

12. The method of claim 10, wherein flowing syngas over the tungstated zirconia comprises flowing the syngas comprising a molar ratio of hydrogen:carbon monoxide of between about 1:1 and about 4:1 over the tungstated zirconia.

13. The method of claim 10, wherein flowing syngas over the tungstated zirconia comprises flowing the syngas comprising a molar ratio of hydrogen:carbon monoxide of between about 1:1 and about 3:1 over the tungstated zirconia.

14. The method of claim 10, wherein flowing syngas over the tungstated zirconia comprises flowing the syngas over the tungstated zirconia at from about 300 standard liters per hour per kilogram (SLPH/kg) of tungstated zirconia to about 1,800 SLPH/kg of tungstated zirconia.

15. The method of claim 10, wherein recovering the product stream comprises separating the at least one light alkene from other hydrocarbon compounds in the product stream.

16. The method of claim 10, wherein heating a precursor of tungstated zirconia in air or nitrogen to a temperature of between about 350° C. and about 550° C. comprises heating a zirconium oxide precursor and a tungsten oxide precursor in air or nitrogen to a temperature of between about 350° C. and about 550° C. to form the tungstated zirconia comprising tungsten oxide on zirconia.

17. A method of producing a light alkene comprising:
heating a precursor of tungstated zirconia to form tungstated zirconia, the tungstated zirconia comprising tungsten oxide at from about 5% by weight to about 17% by weight of a total weight of the tungstated zirconia;
contacting syngas and the tungstated zirconia to produce a product stream comprising at least one light alkene; and
recovering the product stream.

18. A method of producing a light alkene comprising:
contacting a catalyst consisting of tungstated zirconia with syngas produce a product stream comprising at least one light alkene at greater than about 50% by weight of a total weight of the product stream, the at least one light alkene comprising at least one of a $C_2$ alkene, a $C_3$ alkene, or a $C_4$ alkene; and
recovering the product stream.

19. The method of claim 18, wherein contacting a catalyst consisting of tungstated zirconia with syngas to produce a product stream comprising at least one light alkene comprises contacting a catalyst consisting of tungstated zirconia with syngas to produce ethylene, propylene, butylene, or combinations thereof at greater than about 50% by weight of a total weight of the product stream.

20. The method of claim 18, wherein contacting a catalyst consisting of tungstated zirconia with syngas comprises contacting the catalyst consisting of tungstated zirconia with the syngas, the tungstated zirconia consisting of zirconia ($ZrO_2$) and tungsten oxide ($WO_x$), where x is 2 or 3.

* * * * *